United States Patent [19]
Dishler

[11] Patent Number: 6,135,984
[45] Date of Patent: Oct. 24, 2000

[54] CANNULA FOR USE IN CORRECTIVE LASER EYE SURGERY

[76] Inventor: Jon G. Dishler, 6295 S. Macon Way, Englewood, Colo. 80111

[21] Appl. No.: 09/226,376

[22] Filed: Jan. 6, 1999

[51] Int. Cl.[7] ................................................ A61M 5/00
[52] U.S. Cl. .................... 604/264; 604/257; 604/181; 604/187; 606/162
[58] Field of Search ...................... 604/264, 47, 239–243, 604/257, 275, 523, 911, 181, 187; 222/566, 565, 572, 575; 606/162

[56] References Cited

U.S. PATENT DOCUMENTS

| | | |
|---|---|---|
| 10,303 | 12/1853 | Warren . |
| 634,108 | 10/1899 | Henry . |
| 762,603 | 6/1904 | Witkowski . |
| 1,125,887 | 1/1915 | Schimmel . |
| 1,331,271 | 2/1920 | MacGregor . |
| 1,569,174 | 1/1926 | Crowther . |
| 3,439,675 | 4/1969 | Cohen ..................................... 128/239 |
| 3,661,144 | 5/1972 | Jensen et al. ........................... 128/2 B |
| 4,402,684 | 9/1983 | Jessup ..................................... 604/264 |
| 4,432,758 | 2/1984 | Finegold ................................. 604/104 |
| 4,617,018 | 10/1986 | Nishi ..................................... 604/264 |
| 4,813,928 | 3/1989 | Abe et al. ................................ 604/49 |
| 5,356,389 | 10/1994 | Willing .................................... 604/164 |
| 5,423,764 | 6/1995 | Fry ......................................... 604/187 |
| 5,792,099 | 8/1998 | DeCamp et al. ......................... 604/51 |
| 5,817,075 | 10/1998 | Giungo ................................... 604/294 |
| 5,876,379 | 3/1999 | Beauvais et al. ........................ 604/181 |
| 5,997,516 | 12/1999 | Caro et al. .............................. 604/264 |
| 6,024,726 | 12/1999 | Hill ........................................ 604/187 |
| 6,042,572 | 3/2000 | Fowler .................................... 604/239 |
| 6,047,209 | 4/2000 | Denny et al. ............................ 604/21 |

*Primary Examiner*—Sharon Kennedy
*Assistant Examiner*—Chris L. Rodriguez
*Attorney, Agent, or Firm*—Timothy J. Martin; Michael R. Henson; Mark H. Weygandt

[57] ABSTRACT

A cannula for use in conjunction with a fluid source to irrigate a corneal surface of an eye, comprises a connector adapted to attach to the fluid source; and an elongated, hollow prong element having a proximal end supported by said connector and a distal tip opposite proximal end. The prong element includes an arcuate distal section formed in a plane along a curvature and having a fluid passageway therein that is surrounded by a sidewall with the fluid passageway being in fluid communication with the fluid source when the connector is fastened thereto. A port in the distal section of the prong extends from the fluid passageway through the sidewall whereby fluid from the fluid source may be ejected out of the port and onto the corneal surface during use.

36 Claims, 4 Drawing Sheets

CANNULA FOR USE IN CORRECTIVE LASER EYE SURGERY

FIELD OF THE INVENTION

The present invention broadly concerns eye surgery for correcting visual acuity by reforming the cornea by way of removal of tissue underneath a corneal flap, but is particularly directed to the proper postoperative replacement of the corneal flap.

BACKGROUND OF THE INVENTION

The value and need for visual acuity cannot be overstated. Historically, human beings have relied on eyesight as perhaps the most significant sensory perception employed in interacting with the environment. Unfortunately many persons, however, experience slight aberrations in the physical structure of the eye which aberrations interfere with the maximum acuity possible, These aberrations primarily manifest in three conditions: (1) myopia; (2) hyperopia; and (3) astigmatism.

Myopia is a condition wherein parallel light rays entering the eye are focused in front of the retina such that nearby objects are seen with greater clarity than distant objects. Myopia can be caused by an elongated eyeball or by a cornea which has too steep of a curvature resulting in greater refraction than desired. On the other hand, hyperopia is a condition wherein parallel light rays focus behind the retina so that distant objects are seen more clearly than nearby objects. Hyperopia results where the eyeball is foreshortened or where the curvature of the cornea is not steep enough for proper focusing of light rays onto the retina. Astigmatism is a defect of the eye whereby rays of light converge unequally in different meridians thus causing uneven focus or multiple images to be perceived. Astigmatism typically results where the cornea is slightly ovoid instead of circular.

Until the middle ages, people were generally confined to the visual acuity provided by their respective eye physiology. However, greater understanding of optics lead to the creation of corrective lenses which, when placed in front of the eye, could compensate for visual defects thereby causing a redirection of light whereby the defective eye would focus light onto the retina. As the understanding of both optics and eye physiology grew, lenses became more and more sophisticated. In the present day, lenses can correct for myopia, hyperopia, astigmatism and other eye conditions. Lenses are sometimes designed to have different focusing properties in different sections, such as bifocals and trifocals, in order to compensate for different visual acuity of an eye at different distances.

While the invention of eyeglasses may well be one of the most significant contributions to the quality of human life, at least for those who have visual defects, eyeglasses have their drawbacks. For example, eyeglasses provide a generally conic field of vision defined by that volume which is the geometric projection of the perimeter of the lens from the focal point thereof; thus, there is no enhancement of peripheral vision. Moreover, many people find the wearing of eyeglasses to be somewhat uncomfortable, especially if they are not fit properly. Discomfort can result from the weight of the lenses as well as the frame holding them or an improper fit of the frame to the differing shapes of the human head. During times of high activity wherein the need for visual acuity is often greatest, eyeglasses can tend to become dislodged resulting in a loss of visual acuity at a time when it is especially desired. Finally, some persons perceive the wearing of glasses to be aesthetically unpleasing. Unfortunately, the wearer of eyeglasses may sometimes be self-conscious or openly subjected to derisive comments from others.

As a result of the disadvantages of eyeglasses, efforts were made to create lenses which would fit directly onto the eye which would allow greater peripheral vision, which would be more secure and which would be less noticeable to others. Such a lens, commonly referred to as a "contact lens", had their first major development circa 1945. At the time of inception, these lenses were large shells which fit over substantially the entire exposed surface of the eyeball. These early lenses caused substantial irritation to the eye and to the surrounding tissues. Accordingly, they could only be worn for a short period of time.

Over the next two decades, the physical size of contact lenses decreased, and improvements were made in materials technology so that contact lenses came to be made of plastic and were of reduced thickness and diameter. The diameter of the lens was reduced to approximately 8 to 10 millimeters, corresponding to the necessary corrective dimensions needed for the eye over differing light conditions. While these hard plastic lenses were substantial improvements over the earlier glass lenses, they nevertheless still caused irritation and sometimes pain to the wearer. In part this was due to the irritation of the eye and inner surface of the eye lid but it also was a function of diminished oxygen exchange by the lubricating fluids of the eye which were trapped between the eyeball and the lens.

Another avenue investigated for correcting defects in visual acuity has been through eye surgery. Surgery for correcting certain defects in the eye, such as vision obscuring cataracts, dates back approximately two thousand years wherein a needle was inserted into the eye in a manner to dislodge the occluded lens and push it out of the optical path. It was not until the 1960's, however, that significant developments towards surgical correction of the refractive properties of the eye became developed.

One technique pioneered at this time has come to be known as radial keratotomy which can be used to correct mild levels of myopia. In radial keratotomy, the cornea of the eye is slit along a plurality of lines radiating from the pupil with such cuts being made at constant depths. The result is that the cornea relaxes to reduce the steepness of its curvature thereby resulting in a longer focal length. The overall result is that the focal point of the eye is moved rearwardly onto the retina. Radial keratotomy, however, is not available as a treatment for hyperopia since hyperopia requires the creation of a greater lensing effect. Similar in concept to radial keratotomy is astigmatic keratotomy wherein arcuate slits are selectively cut into the eye at desired radial distances so that the ovoid configuration of the cornea becomes more round.

Somewhat contemporaneously with the development of radial keratotomy was the investigation into a technique that became known as, lamellar refractive surgery. A first developed technique was myopic keratomileusis (MKM). Here, a surgeon would cut a dome-like shell or cap off of the cornea and remove a disk of corneal tissue after which the cap was replaced. The removal of the cornea tissue reduced the steepness of the corneal curvature thereby lessening its lensing effect resulting in correction of a myopic condition. This technique had three main drawbacks. First, proper rotational orientation of the corneal cap on replacement was difficult. Second, even after the repositioning of the corneal cap, it was subject to dislodgement and possible loss during the healing process. Third, and significantly, it was difficult for a surgeon to manually cut a uniform disk out of the cornea. Any anomalies in the thickness of the removed disk created non-uniform correction.

Two major advances helped establish MKM as a viable corrective technique. First, the rotational issue of the corneal cap was resolved by developing a technique wherein the dome-like cap was not cut completely off of the cornea but was rather left attached by a small hinge of tissue along one edge. During surgery, this cap was then pivoted out of the way while the corrective tissue disk was removed from the cornea after which the cap was repositioned. The tissue hinge maintained proper orientation and also helped decrease the likelihood of dislodgement and loss of the corneal cap during the healing process. Second, advances in computer technology and better instrumentation resulted in the development of the automated microkeratome. This device, in essence, is an automated scalpel which could be computer controlled to cut a fairly uniform thickness disk out of the cornea after the corneal cap had been cut and pivoted out of position. This could be accomplished directly on the globe portion of the eye and therefore avoid the necessity of freezing the corneal cap as had been the case with MKM. This operative procedure came to be known as automated lamellar keratoplasty (ALK) and its use became more accepted in the late 1980's. This technique was advantageous for its ability to correct more extreme cases of myopia.

Next in the development of surgical techniques for corrective eye surgery was the laser technique known as the excimer laser technique. In this technique, the surface of the cornea is burnt away in a desired configuration by a light intensity laser beam operating at 193 micron wavelength. The laser beam is controlled in intensity and pattern to etch away surface corneal tissue so as to alter its curvature and thereby its refractive properties in order to correct myopic and astigmatic conditions.

The excimer laser is a somewhat painful process, though, since it burns away the epithelia layer which requires one to two weeks to heal. In addition, the excimer laser sometimes causes undesired scarring of the cornea. The excimer laser, however, does show substantial promise for correcting mild to medium myopia and astigmatism.

Recently, however, perhaps the most promising of all surgical techniques has been explored using a combination of automated lamellar keratoplasty and the benefits of excimer-type lasers. This procedure, which is known as laser assisted intrastromal keratomileusis (LASIK) involves the cutting of the dome-like corneal cap utilizing the microkeratome. After cutting the cap, the microkeratome is removed from the support assembly and the cap is pivoted out of position. Laser focusing optics are then brought into position over the exposed, domed surface of the cornea formed by removal of the cap shell. The laser light is then very precisely controlled so that a desired contoured shaping of the exposed surface occurs by varying the tracking, intensity and size of the laser beam. After performing the sculpting of the corneal interior, the cap is repositioned and the cornea reheals with a modified curvature.

LASIK surgery is especially promising in that it provides numerous advantages over previous surgical techniques. On one hand, the use of a laser surgical technique can be very precisely controlled, as is the case with traditional excimer surgery, so that the cutting of the proper corrective contour can be very precise. In addition, since the removal of tissue occurs in the inside of the cornea, the epithelial layer and the Bowman's layer are not removed so that very little pain and less damage to the cornea occurs. The ability to control the laser also allows for the simultaneous correction of both the necessary refractive prescription as well as correction of astigmatism. The LASIK technique also has the benefit of being able to correct severe degrees of myopia up to approximately 30 diopters. Finally, unlike many of the other techniques, the LASIK procedure holds great promise for its ability to correct hyperopia as well as myopia.

One issue of concern in LASIK, as well as in ALK, procedures is the manner in which the dome-like corneal cap is repositioned onto the cornea after the corneal-sculpting procedure is performed. Particles such as dust from the air or loose tissue particles remaining after the cornea is sculpted must be removed from between the cornea and the corneal flap, such as by irrigation, after repositioning the flap onto the eye. Also, the flap must be drawn across the eye so as to make a seal and prevent wrinkling of the corneal flap.

A device currently used in the repositioning of the flap is called a cannula. The cannula generally is a single-use or multi-use needle-like structure which can be attached to a syringe. The syringe can hold fluid useful in irrigating the eye to remove particles after repositioning the flap onto the cornea. Generally, the cannula is a tubular structure open at both ends so that fluid may flow from the syringe through the cannula and onto the eye. One end portion of the cannula is connectably attached to the syringe by an engaging mechanism. The other end portion is open at the distal end. The cannula may be a straight tube or may be bent so as to extend at an angle from the longitudinal direction of the syringe.

After the flap is returned to the cornea, the cannula is inserted between the cornea and the flap. The syringe plunger is depressed so as to force fluid through the cannula onto the eye, thus irrigating the interface between the cornea and the flap and causing the removal of any particles trapped in the interface. The cannula is then drawn across the cornea so as to squeeze any excess fluid out of the interface and to draw the flap into proper position.

Many problems exist regarding the use of cannulas of the structure described above. Difficulties are encountered with the attempted insertion of the cannula underneath the flap and into the interface between the cornea and the flap. The distal end of the cannula may be sharp enough to cause poking of the eye resulting in damage to the eye. Fibers in the interface between the flap and the cornea may catch on the sharp end of the cannula resulting in further damage to the eye. Further, fluid may flow onto the eye from the distal end of the cannula at a rate and pressure greater than that desired.

In any event, it can be appreciated that there remains a need for an improved device for irrigating and repositioning the cornea flap onto the cornea after corneal-sculpturing has been performed in corrective eye surgery procedures such as LASIK and ALK. The present invention is directed toward such need and this invention concerns a device for irrigating and repositioning a corneal flap onto a cornea after various methods of corrective eye surgery.

SUMMARY OF THE INVENTION

It is an object of the present invention to provide a new and useful cannula which may be used in corrective eye surgery procedures.

Another object of the present invention is to provide an apparatus effective in repositioning a corneal flap after eye surgery procedures such as LASIK and ALK.

Another object of the present invention is to provide an apparatus for irrigating a cornea and corneal flap to remove particles therefrom.

Another object of the present invention is to provide an apparatus to gently squeeze away excess fluid on a cornea so as to allow a corneal flap to float into correct position.

A further object of the present invention is to provide a safe cannula device which will prevent poking and snagging of corneal tissue.

A further object of the present invention is to allow complete irrigation of the corneal interface with minimal fluid and flow pressure.

In accordance with these objectives, the present invention is in one sense directed to a cannula for use in conjunction with a fluid source for irrigating a corneal surface of an eye. The present invention also relates to an apparatus adapted for use in irrigating the corneal surface during surgical procedures thereon, wherein the apparatus incorporates a conventional syringe body and the cannula discussed hereinbelow.

In its broadest form, the cannula includes a connector adapted to attach to the fluid source and an elongated, hollow prong element. The prong element has a proximal end supported by the connector and a distal tip opposite the proximal end. The prong element includes an arcuate distal section formed in a plane along a curvature and has a fluid passageway therein which is surrounded by a sidewall so that the fluid passageway is in fluid communication with the fluid source when the connector is fastened thereto. The prong element also has at least one port in the distal section that extends from the fluid passageway through the sidewall whereby fluid from the fluid source may be ejected out of the port and onto the corneal surface during use.

The connector is adapted to mount onto a connector tip of a conventional syringe that contains the fluid source, and both the connector and the prong element may be integrally constructed of a polymeric material. Alternatively, the connector may be composed of polymeric material and the prong element may be composed of metal.

The distal tip of the prong element is preferably rounded and closed and it is preferred that a plurality of ports be formed in its distal section, with each of these ports extending from the fluid passageway through the sidewall. Preferably, adjacent ones of these ports are equidistantly spaced from one another with at least two of the ports opening toward opposite sides of the plane of the distal section and diametrically opposite one another. It is also preferred that a greater number of these ports open toward a first side of the distal section's plane as compared to the number of ports opening toward a second side of the distal section's plane. The ports may be circular in cross-section with each having a diameter of approximately 0.14 millimeters. Regardless of the number of ports employed, the ports are operative to eject fluid in an ejection direction that is transverse to the plane of the distal section and at an ejection angle between about 70° and 90°, inclusively.

The prong element includes a linear proximal section oriented along a longitudinal axis with this proximal section and the distal section being connected at a juncture. The distal section and this juncture may be separated by an arc of between about 43° and 55°, corresponding to approximately 0.75 radians and 0.96 radians, respectively. Preferably, the distal section is canted with respect to the proximal section such that a line extending through the juncture and the distal tip is oriented at an obtuse angle that may be between about 110° and 140°, inclusively, with respect to the proximal section. Moreover, the distal section is preferably formed along a radius of curvature of between about 9.0 millimeters to 10.3 millimeters, inclusively.

Where the present invention is directed to an apparatus for irrigating the corneal surface during surgical procedures, this apparatus broadly includes a syringe body, a plunger and a cannula. The cannula incorporates the features discussed above. As with a conventional syringe, the syringe body includes an elongated hollow barrel having a barrel interior surrounded by a barrel sidewall. An opening is located at a first end of the syringe body and a connector tip is located opposite this opening. The connector tip has a bore therethrough which is in fluid communication with the barrel interior. The plunger is received in the barrel interior and is movable therein between a withdrawn position and a depressed position so that when the plunger is in the withdrawn position the fluid received in the barrel interior may be ejected out of the port(s) of the prong element and onto the corneal surface by moving the plunger toward the depressed position.

These and other objects of the present invention will become more readily appreciated and understood from a consideration of the following detailed description of the exemplary embodiments when taken together with the accompanying drawings, in which:

DETAILED DESCRIPTION OF THE EXEMPLARY EMBODIMENT

The present invention is directed to a cannula which can be used in eye surgeries, such as LASIK and ALK, to irrigate the corneal surface of an eye and to reposition a corneal flap cut for such surgeries. The present invention is also directed to an apparatus adapted for use in irrigating a corneal surface during surgical procedures thereon, which apparatus comprises a conventional syringe and a cannula constructed according to any one of the various embodiments described herein. Specifically, the present invention is directed to a cannula for use in conjunction with a fluid source, such as a syringe. The cannula has a connector adapted to fasten to the fluid source and a prong element secured to the connector. The prong element is preferably sized and adapted to follow the outer curvature of a patient's cornea, such that a portion of the sidewall of the prong element is coextensive with the outer surface of the cornea. The cannula may be mountable on a syringe, but it should be understood that the cannula may be used with other fluid sources.

Figure 1:
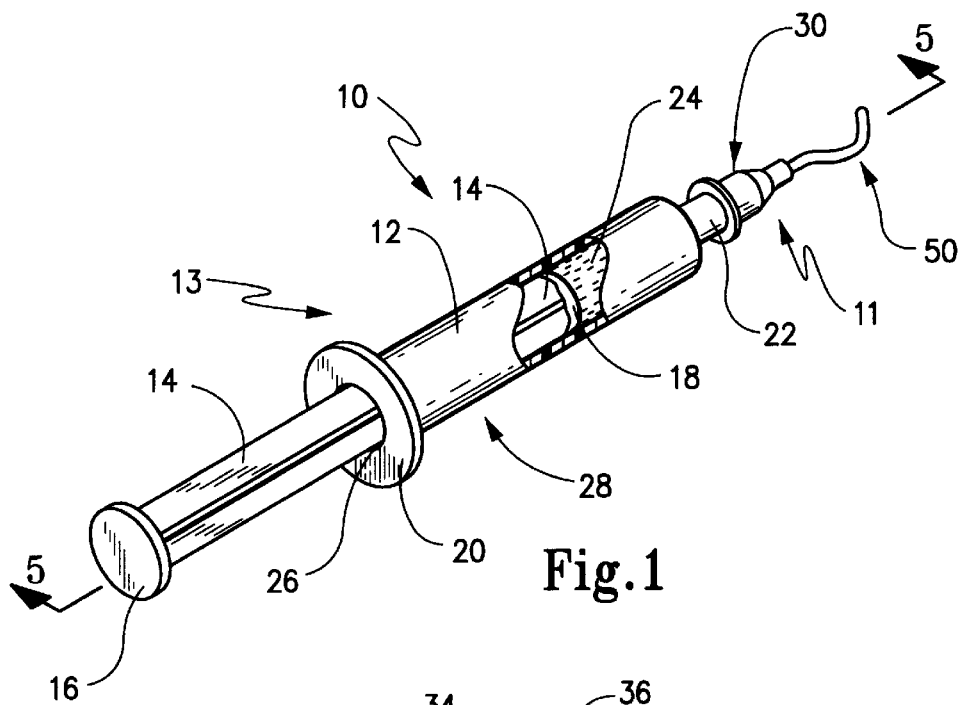
FIG. 1 is a perspective view of a conventional syringe incorporating a cannula according to the first exemplary embodiment of the present invention to form the apparatus of the present invention, with the syringe partially broken-away to reveal its plunger in a partially withdrawn position.

As generally introduced in FIG. 1, it may be seen that an irrigation apparatus 10 comprises a conventional syringe 13 and a cannula 11 constructed according to a first exemplary embodiment of the present invention. Cannula 11 is connected to syringe 13 in fluid communication therewith. Cannula 11 broadly includes connector 30 and prong element 50. Syringe 13 includes a syringe body 28 and a plunger 14 slidably disposed therein. In this embodiment, syringe 13 is operational as a fluid source for cannula 11.

Figure 2:
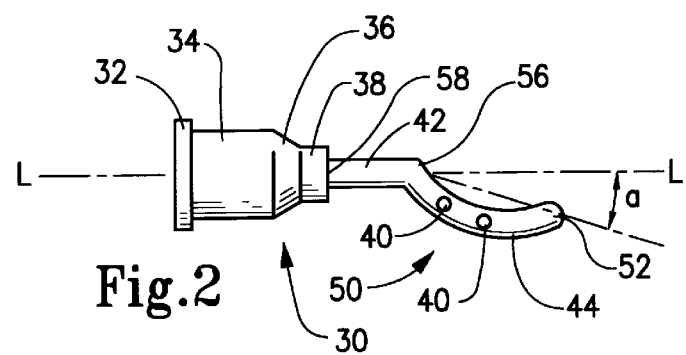
FIG. 2 is a side view in elevation showing the cannula of FIG. 1.
Figure 3:
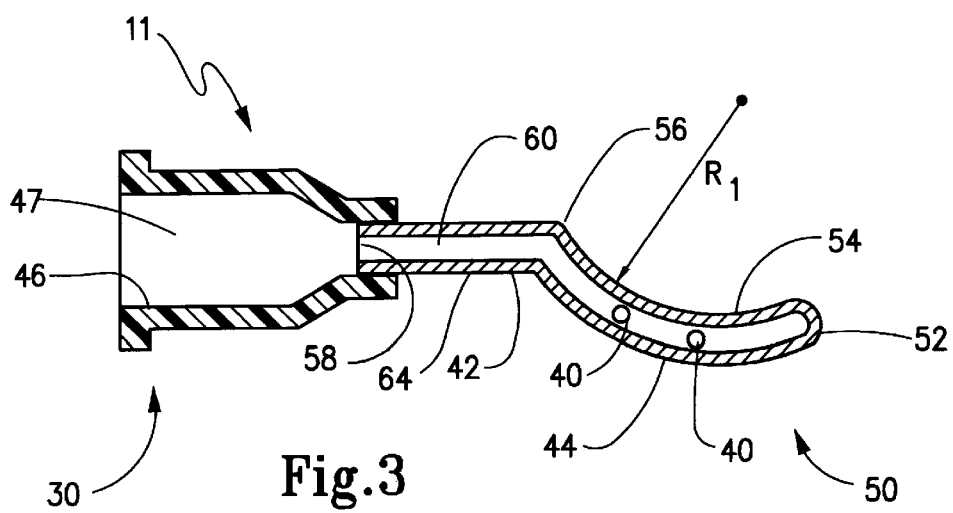
FIG. 3 is an enlarged side view in cross-section of the cannula shown in FIGS. 1 and 2.
Figure 4:
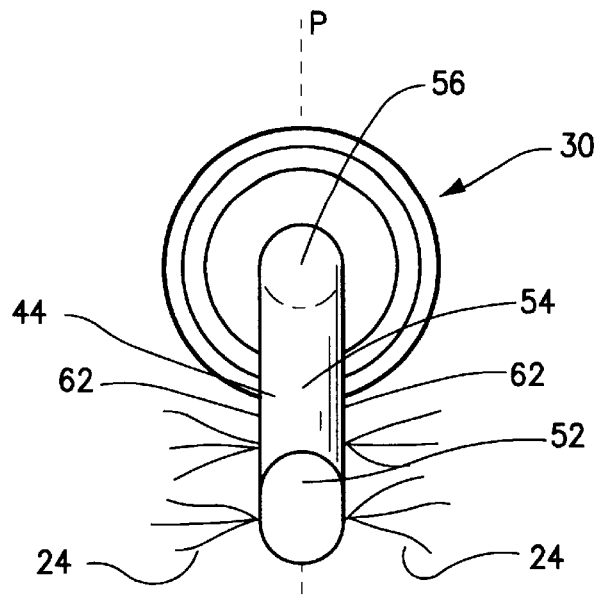
FIG. 4 is a front end view in elevation of the cannula of FIGS. 2 and 3, and illustrating the ejection of fluid therefrom.

Cannula 11 is shown in greater detail in FIGS. 2 through 4. With reference to FIG. 2, connector 30 is generally in the form of a tapered hub that is cylindrical in cross section in order to channel fluid flowing from syringe 13 into prong element 50. To this end, connector 30 may be integrally constructed to include a flange 32 which is adapted to abut syringe 13. Joined to flange 32 and extending dowstream therefrom is large tubular portion 34, a tapered portion 36 and a small tubular portion 38. Small tubular portion 38, as best shown in FIG. 3, is sized and adapted to support a proximal end 58 of prong element 50 by frictional fit. The ordinarily skilled person will appreciate that other manners of connection may be employed, such as snap fits, adhesion, threading, etc., all as generally known in the art. Connector 30 may be composed of varying alternative configurations of one or a plurality of fixedly connected tubular portions adapted to fasten to a fluid source in fluid communication therewith.

In the first exemplary embodiment, prong element 50 includes a proximal section 42 that is linear and is disposed adjacent to connector 30 in fluid communication therewith and projecting therefrom along longitudinal axis "L". It should be noted that proximal section 42 may be non-linear. A distal section 44 is arcuate and formed in a plane "P" (FIG. 4) along a curvature $R_1$ (FIG. 3). Preferably, the proximal section is linear and oriented along a longitudinal axis "L". Distal section 44 is connected to proximal section 42 at a juncture 56; however, it should be understood that prong element 50 may be entirely arcuate in configuration.

In the first exemplary embodiment, distal section 44 has a plurality of ports 40, which extend from the fluid passageway 60 through the sidewall 64. Distal section 44 terminates at a distal tip 52, which is shown as closed and rounded or blunt, but which may also be open. Ports 40 may open toward a common side of the plane of the distal section. In this embodiment, the distal tip of the prong element is canted relative to the proximal section. To illustrate, a line drawn through distal tip 52 and juncture 56 extends transversely to longitudinal axis "L" at an acute angle "a" relative to "L", and is oriented at an obtuse angle with respect to the proximal section. Such obtuse angle may be between about 110° to 140°, inclusively.

As is shown in FIG. 3, arcuate distal section 44 has a radius of curvature $R_1$, to match the normal curvature of a human cornea. $R_1$ is preferably between approximately 9.0 millimeters and 10.3 millimeters, although other radii of curvature are contemplated. The linear length of the arcuate distal section 44 from juncture 56 to distal tip 52 may vary, with lengths such as 7 millimeters and 9 millimeters contemplated. The larger size may be more effective in certain surgical procedures utilizing a larger corneal flap.

It may be seen that a margin of proximal section 42 may extend interiorly of connector 30 to abut the interior surface 46 of connector 30. As such, the first passageway 47 of connector 30 is in fluid communication with the fluid passageway 60 of prong element 50, where fluid passageway 60 is disposed within prong element 50 and is defined by sidewall 64.

Ports 40 may have an approximate diameter of 0.14 millimeters. Adjacent ones of these ports 40 may be separated by approximately 10° of arc along distal section 44. Adjacent ports may be equidistantly spaced from one another.

Sidewall 64 may be composed of various gauges of metal, and connector 30 may be composed of polymeric or other material. Arcuate distal section 44 may be of a smaller size having a linear length of between approximately 6.6 and 7.5 millimeters from distal end 52 to juncture 56. This length corresponds to approximately 0.75 radians along distal section 44 from a circle having radius $R_1$ of between about 9.0 millimeters to 10.2 millimeters. Alternatively, distal section 44 may be of a larger size having a linear length of between 8.4 and 9.5 millimeters from distal end 52 to juncture 56. This length corresponds to approximately 0.96 radians along distal section 44 from a circle having radius "$R_1$" of between about 9.1 millimeters and 10.3 millimeters. Other lengths, radii and angles of arc are contemplated. The diameter of prong element 50 may be approximately 0.4 millimeters, although alternative diameters are contemplated.

It may be seen from FIG. 4 that fluid may be ejected through ports 40 which may open toward opposite sides of the plane "P" of the distal section 44. Ports 40 may be operative to eject fluid in an ejection direction that is at a large acute ejection angle with respect to the plane "P" of distal section 44. Preferably, the ejection angle is between about 70° and 90°, inclusive. The use of a plurality of ports extending from the passageway through the sidewall allows fluid from the fluid source to be ejected out of the port and onto the corneal surface with a minimal amount of fluid and fluid pressure so as to irrigate the interface between the cornea and the corneal flap. The ports may be situated in various relation to each other, such as on common sides of the distal section, opposite sides, equidistantly spaced, diametrically opposed, or other relative positioning.

Figure 5:
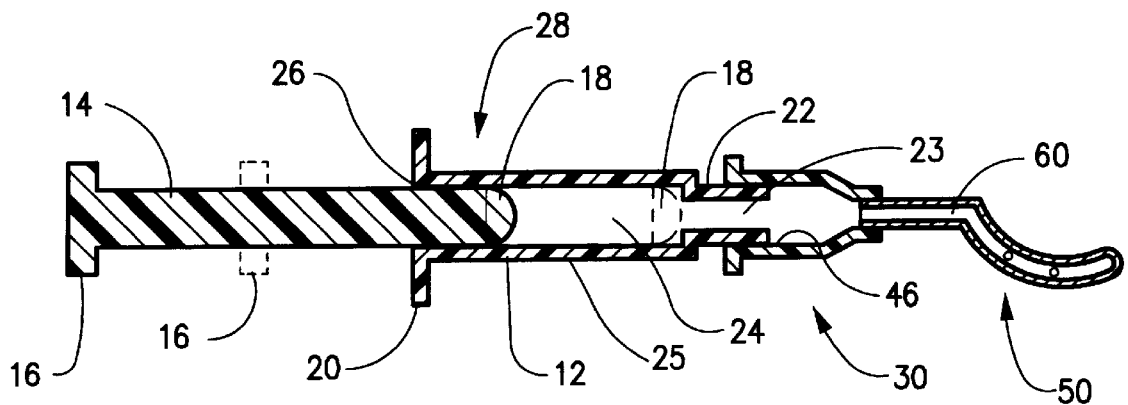
FIG. 5 is a cross-sectional view of the apparatus of the present invention as viewed about lines 5—5 in FIG. 1 and shows the plunger in a withdrawn position and deployed position (in phantom)

The syringe structure is best shown in FIG. 5. Here, syringe body 28 has an elongated hollow barrel 25 having a barrel interior 24 surrounded by a barrel sidewall 12. The syringe body 28 has an opening 26 at a first end thereof and a connector tip 22 opposite the opening, the connector tip 22 having a bore 23 therethrough in fluid communication with the barrel interior 24 and first passageway 47 of connector 30. A plunger 14 is received in the barrel interior 24, having a plunger head 16. A rubber bulb 18 attached to the plunger 14 is operative to contact fluid in the barrel interior 24. A finger flange 20 may be disposed on syringe body 28. The connector tip 22 is operative to secure connector 30 to syringe body 28. An elongated, hollow prong element 50 is secured to connector 30. Prong element 50 has a fluid passageway 60 that is in fluid communication with the fluid source, which in this case is barrel interior 24, when connector 30 is connected to connector tip 22. By moving plunger 14 from a withdrawn position to a depressed position, shown in phantom, rubber ball 18 pressures liquid in barrel interior 24 thereby forcing the liquid into prong element 50.

As shown in FIG. 5, the cannula 11 may be mountable on the syringe or other fluid source by engagement of the connector 30 with the connector tip 22 of the syringe or other fluid source. It is contemplated that connectors of the leur-lock type known in the art may be used, or connectors using friction, screw-threading, or other connection methods may be used to fixedly attach the cannula 11 to the fluid source. In the first exemplary embodiment, inner connector surface 46 frictionally contacts connector tip 22 in such a manner as to securely engage syringe body 28. It should be understood that connectors of alternate configurations are contemplated, including those which may contact the syringe or other fluid source by the outer surface of connector 30, rather than by an inner surface. For example, connectors are contemplated of the needle hub and locking syringe tip variety, wherein a needle hub is inserted into the cavity of the locking syringe tip, so as to secure the hub and prong element in fluid communication with the barrel interior of the syringe.

Figure 6:
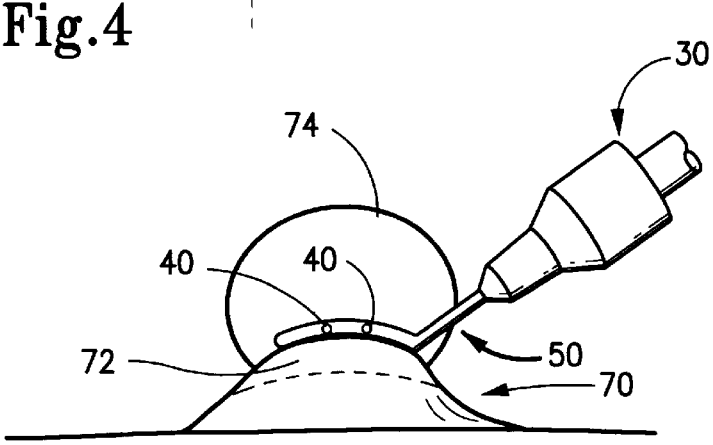
FIG. 6 is a side view in elevation showing how the cannula according to the first exemplary embodiment of the present invention may be employed to irrigate the corneal surface of an eye during a surgical procedure.

As shown in FIG. 6, the manner of use of the device is to place prong element 50 on eye 70 and to move prong element 50 in a plane across cornea 72 following the curvature of cornea 72 while irrigating cornea 72 by depressing plunger 14. Cornea 72 is irrigated by forcing fluid through connector 30 into prong element 50 and out of ports 40 while moving prong element 50 across cornea 72. Such irrigation may occur before and after replacing corneal flap 74 back on cornea 72. The cannula may be used so as to gently squeeze any excess fluid out of the interface between cornea 72 and corneal flap 74 and to draw the corneal flap 74 across the cornea 72 allowing the corneal flap to float into the correct position. Configuring distal tip 52 to be rounded or blunt prevents snagging on corneal tissue, and is especially useful in retreatment cases where the corneal surface may be more fragile.

The proximal section may be useful to provide additional operating distance between the arcuate distal section 44 and the fluid source. The canting of the arcuate distal section with respect to the proximal section further provides ease of use and operative distance during surgical procedures on the eye. The gauge of prong element 50 may vary. The preferred gauge is a 30 gauge prong element, which is small in diameter so as to provide some flexing of the cannula which provides a gentler apposition of the corneal flap to the bed of the corneal surface. Other gauges may range from 22 to 27 gauge, with additional gauges contemplated. A contact surface 54 of arcuate distal section 44 is curved so as to follow the outer curvature of a patient's cornea. It is contemplated that ports 40 may be disposed on contact surface 54. Ports 40 may be otherwise positioned on the arcuate distal section 44, and may provide multiple streams of fluid to be ejected onto the corneal surface. This allows complete irrigation of the interface between the flap and the corneal surface with minimal fluid pressure and allows the flap to float into the correct position. When plunger 14 is moved into a depressed position from a withdrawn position, fluid from the barrel interior may be moved through the passageway and ejected out of the port or ports and onto the corneal surface.

Figure 7:
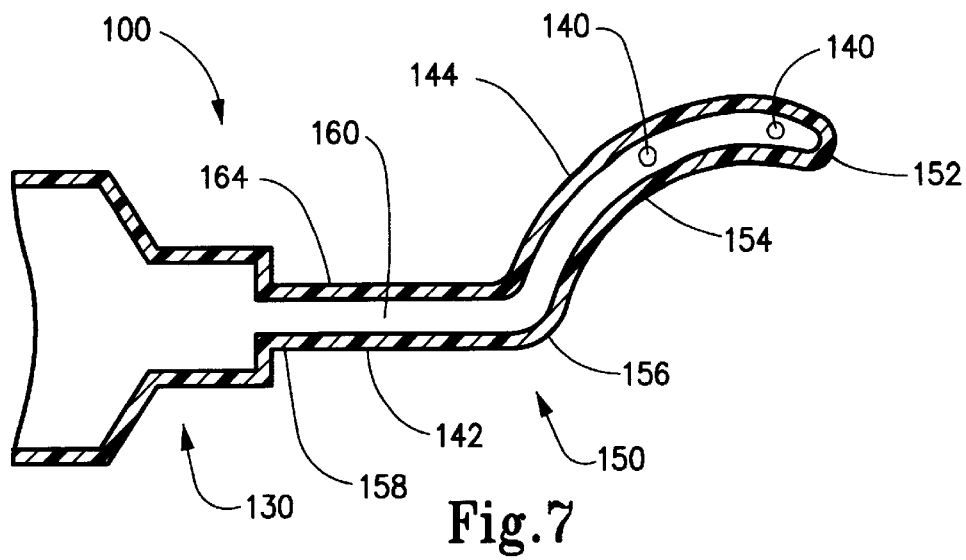
FIG. 7 is a side view in elevation, and in cross-section, of the cannula according to a second exemplary embodiment of the present invention.

A second exemplary embodiment 100 is shown in FIG. 7. In this embodiment, connector 130 joined to prong element 150 at proximal end 158 of prong element 150 is shown as a one-piece construction. The device may be constructed of metal or a polymeric or other material. This embodiment may be multi-use or single-use disposable. Fluid passageway 160 is shown disposed within prong element 150 and is defined by sidewall 164. Proximal section 142 is attached to distal section 144 at juncture 156. Contact surface 154 is disposed on distal section 144 as are ports 140. Distal section 144 terminates in distal tip 152 which is rounded in shape.

Figure 8:
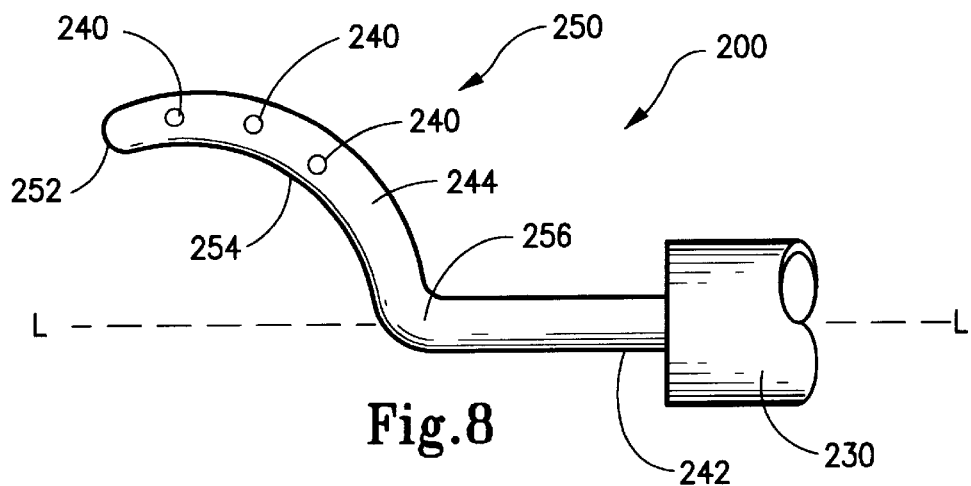
FIG. 8 is a side view in elevation of the cannula according to a third exemplary embodiment of the present invention.

A third exemplary embodiment 200 is shown in FIG. 8. Connector 230 is connected to prong element 250. Proximal section 242 is proximately connected to connector 230. Proximal section 242 connects to distal section 244 at juncture 256. Distal section 244 terminates at distal tip 252 which is rounded in shape. In this embodiment a plurality of ports 240 are disposed on distal section 244.

Figure 9:
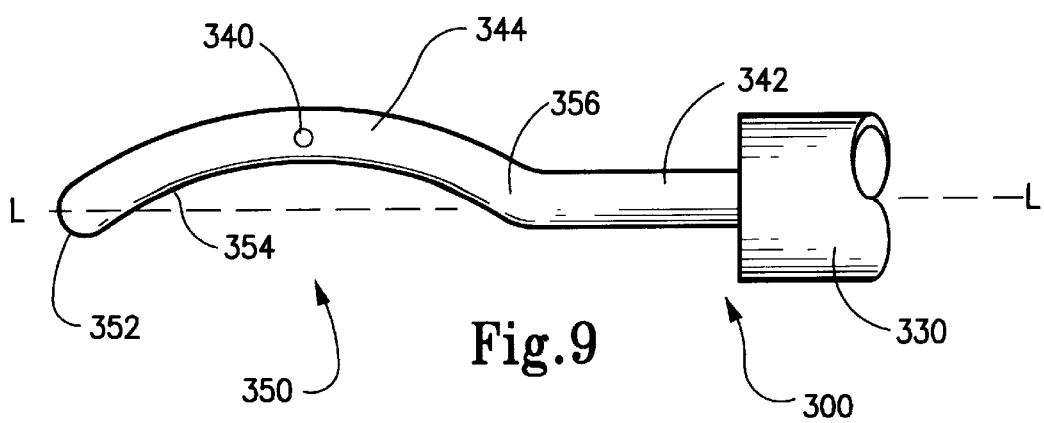
FIG. 9 is a right side view in elevation of the cannula according to a fourth exemplary embodiment of the present invention.
Figure 10:
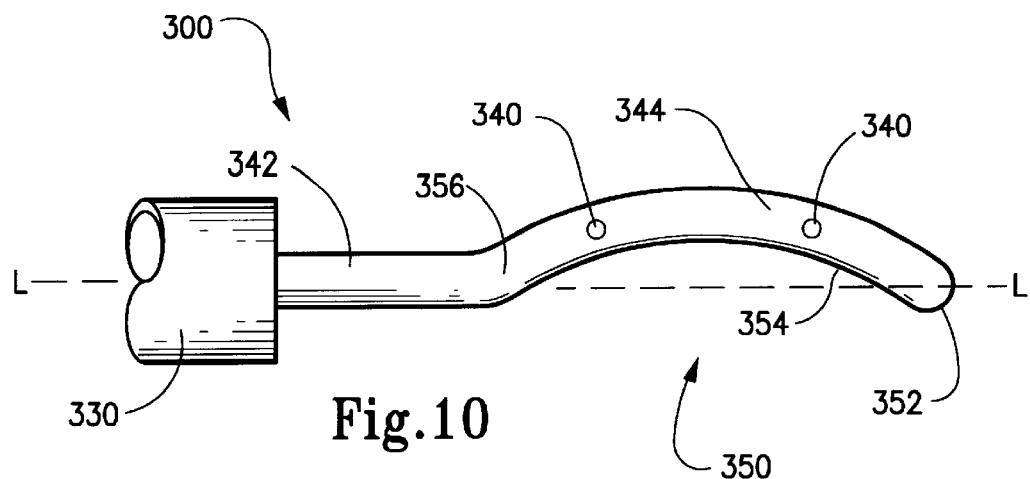
FIG. 10 is a left side view in elevation of the cannula shown in FIG. 9.

A fourth exemplary embodiment is shown in FIGS. 9 and 10. In this embodiment connector 330 proximately connects to prong element 350 at proximal section 342. Distal section 344 connects to proximal section 342 at juncture 356. Distal section 344 terminates in distal tip 352. In this embodiment distal tip 352 is approximately disposed in line with longitudinal axis "L", such that distal section 344 is not canted relative to proximal section 342. Ports 340 may vary in number and be disposed on diametrically opposed sides. Ports 340 may further be juxtaposed rather than directly opposed on opposite sides of the device.

Figure 11:
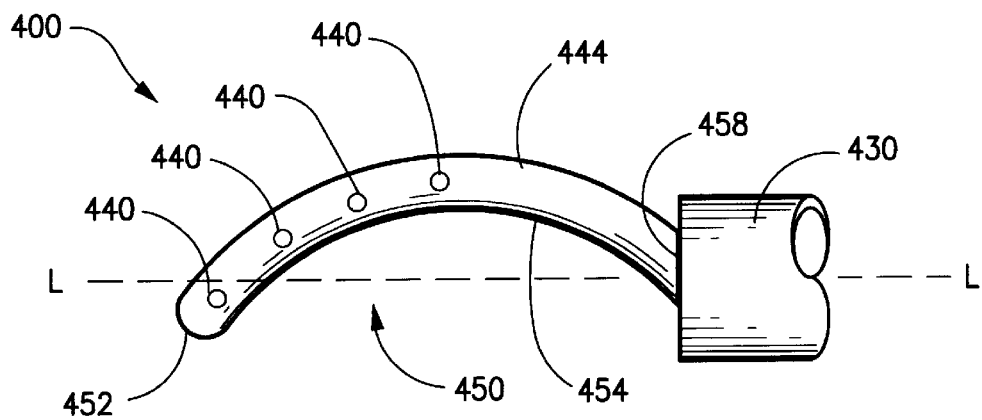
FIG. 11 is a side view in elevation of the cannula according to a fifth exemplary embodiment of the present invention.

A fifth embodiment is shown in FIG. 11 where connector 430 connects to distal section 444 at proximal end 458 of distal section 444. In this embodiment distal section 444 directly contacts connector 430. Distal tip 452 is approximately in line with longitudinal axis "L", such that distal section 444 is not canted relative to longitudinal axis "L" or connector 430. Prong element 450 consists entirely of distal section 444 having ports 440 and contact surface 454. A plurality of ports disposed on one side or diametrically opposed sides of distal section 444 is contemplated.

Figure 12:
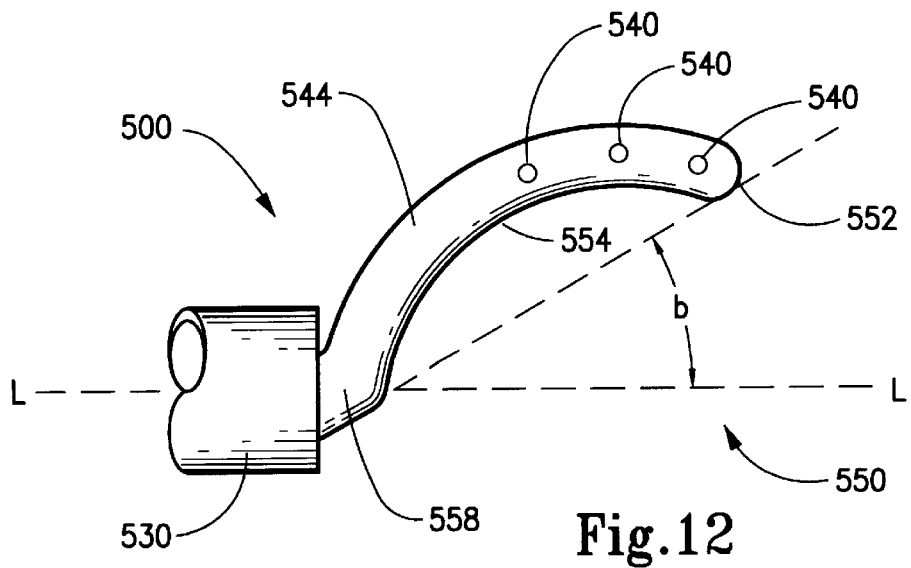
FIG. 12 is a side view in elevation of the cannula according to a sixth exemplary embodiment of the present invention.

A sixth exemplary embodiment 500 is shown in FIG. 12. In this embodiment, connector 530 is proximately attached to distal section 544 at proximal end 558 of distal section 544. Prong element 550 consists entirely of distal section 544 having ports 540, contact surface 554, and distal tip 552. In this embodiment a line running through distal tip 552 and proximal end 558 extends transversely from longitudinal axis "L" at an angle "b", such that distal section 544 is canted relative to longitudinal axis "L" and connector 530. Angle "b" may be approximately 30°.

From the foregoing, it should be appreciated that a variety of embodiments are contemplated which vary the number and positioning of ports, the shape and position of the distal section relative to the longitudinal axis, the material of which the cannula is composed, and other variations as suggested herein.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A cannula for use in conjunction with a fluid source and operative to irrigate a corneal surface of an eye, comprising:
   (a) a connector adapted to attach to the fluid source, said connector oriented along a longitudinal axis; and
   (b) an elongated hollow prong element having a proximal end supported by said connector and a distal tip opposite said proximal end, said prong element preformed to include an arcuate distal section formed in a plane along a curvature, wherein a contact surface of said arcuate distal section is oriented toward said longitudinal axis, said contact surface having a portion thereof which is adapted to be coextensive with the corneal surface of an eye, and wherein said prong element has a fluid passageway therein that is surrounded by a sidewall with the fluid passageway being in fluid communication with the fluid source when said connector is fastened thereto, said prong element having a port in said distal section that extends from the fluid passageway through said sidewall whereby fluid from the fluid source may be ejected out of the port and onto the corneal surface during use.

2. A cannula according to claim 1 wherein said connector is adapted to mount on a connector tip of a syringe that contains the fluid source.

3. A cannula according to claim 1 wherein said prong element has a plurality of ports in said distal section, each of the ports extending from the passageway through said sidewall.

4. A cannula according to claim 3 wherein adjacent ones of the ports are equidistantly spaced from one another.

5. A cannula according to claim 3 wherein at least two of the ports open toward opposite sides of the plane of said distal section.

6. A cannula according to claim 5 wherein at least two of the ports are diametrically opposite one another.

7. A cannula according to claim 3 wherein at least two of the ports open toward a common side of the plane of said distal section.

8. A cannula according to claim 3 having a greater number of ports opening toward a first side of the plane of said distal section relative to the number of ports opening toward a second side of the plane of said distal section.

9. A cannula according to claim 3 wherein said ports are circular in cross-section.

10. A cannula according to claim 9 wherein each of the ports has a diameter of approximately 0.14 millimeters.

11. A cannula according to claim 1 wherein the port is operative to eject fluid in an ejection direction and at an ejection angle that is at a large acute angle relative to the plane of said distal section.

12. A cannula according to claim 11 wherein the ejection angle is between about 70° and 90°, inclusively.

13. A cannula according to claim 1 wherein said prong element includes a linear proximal section oriented along said longitudinal axis with said proximal section and said distal section being connected at a juncture.

14. A cannula according to claim 13 wherein said distal tip and said juncture are separated by an arc of between about 0.75 radians and 0.96 radians.

15. A cannula according to claim 13 wherein said distal section is canted with respect to said proximal section such that a line extending through said juncture and said distal tip is oriented at an obtuse angle with respect to the proximal section.

16. A cannula according to claim 15 wherein the obtuse angle is between about 110° and 140°, inclusively.

17. A cannula according to claim 1 wherein said distal section is formed along a radius of curvature of between about 9.0 millimeters to 10.3 millimeters, inclusively.

18. A cannula according to claim 17 wherein said prong element has a plurality of ports in said distal section, each of the ports extending from the passageway through said sidewall and adjacent ones of the ports being separated by about 10° of arc.

19. A cannula according to claim 1 wherein said prong element is circular in cross-section.

20. A cannula according to claim 1 wherein said distal tip is closed.

21. A cannula according to claim 20 wherein said distal tip is rounded.

22. A cannula according to claim 1 wherein said connector is composed of polymeric material and said prong element is composed of metal.

23. A cannula according to claim 1 wherein said connector and said prong element are integrally constructed of a polymeric material.

24. A cannula according to claim 1 wherein said arcuate distal section is formed along a fixed radius of curvature.

25. A cannula according to claim 1 wherein said prong element is rigid.

26. An apparatus adapted for use in irrigating a corneal surface during surgical procedures thereon, comprising:
   (a) a syringe body including an elongated hollow barrel having a barrel interior surrounded by a barrel sidewall, an opening at a first end thereof and a connector tip opposite the opening, said connector tip having a bore therethrough in fluid communication with the barrel interior;
   (b) a plunger received in the barrel interior and moveable therein between a withdrawn position and a depressed position; and
   (c) a cannula supported by said connector tip and including:
      (i) a connector oriented along a longitudinal axis and having a first passageway therethrough and adapted to mount to the connector tip in fluid communication with the bore thereof; and
      (ii) an elongated hollow prong element having a proximal end secured to said connector and a distal tip opposite the proximal end, said prong element preformed to include an arcuate distal section formed in a plane along a curvature and defined by a radius in said plane that passes through said longitudinal axis, said prong element having a fluid passageway therein that is surrounded by a prong element sidewall, with the fluid passageway being in fluid communication with the barrel interior when said connector is fastened to the connector tip and having a port in said distal section that extends from the fluid passageway through said prong element sidewall whereby fluid received in the barrel interior when said plunger is in the withdrawn position may be ejected out of the port and onto the corneal surface by moving said plunger toward the depressed position.

27. An apparatus according to claim 26 wherein the prong element is sized and adapted to follow the outer curvature of a cornea.

28. An apparatus according to claim 26 wherein the prong element includes a proximal section oriented along said longitudinal axis, with said proximal section and said distal section being connected at a juncture.

29. An apparatus according to claim 28 wherein the distal section is canted with respect to said proximal section such that a line extending through said juncture and said distal tip is oriented at an obtuse angle with respect to said proximal section.

30. An apparatus according to claim 28 wherein said proximal section is linear.

31. A cannula for use in conjunction with a fluid source and operative to irrigate a corneal surface of an eye, comprising:
   (a) a connector adapted to attach to the fluid source, said connector oriented along a longitudinal axis; and
   (b) an elongated hollow prong element having a proximal end supported by said connector and a distal tip opposite said proximal end, said prong element including an arcuate distal section formed in a plane along a curvature and defined by a radius in said plane that originates on one side of said longitudinal axis and terminates on an opposite side of said longitudinal axis, said prong element having a fluid passageway therein that is surrounded by a sidewall with the fluid passageway being in fluid communication with the fluid source when said connector is fastened thereto, said prong element having a port in said distal section that extends from the fluid passageway through said sidewall whereby fluid from the fluid source may be ejected out of the port and onto the corneal surface during use.

32. A cannula according to claim 31 wherein said radius is of a fixed length.

33. An apparatus adapted for use in irrigating a corneal surface during surgical procedures thereon, comprising:
   (a) a syringe body including an elongated hollow barrel having a barrel interior surrounded by a barrel sidewall, an opening at a first end thereof and a connector tip opposite the opening, said connector tip having a bore therethrough in fluid communication with the barrel interior;
   (b) a plunger received in the barrel interior and moveable therein between a withdrawn position and a depressed position; and
   (c) a cannula supported by said connector tip and including:
      (i) a connector having a first passageway therethrough and adapted to mount to the connector tip in fluid communication with the bore thereof; and
      (ii) an elongated hollow prong element having a proximal end secured to said connector and a distal tip opposite the proximal end, said prong element preformed to include a linear proximal section connected at a juncture to an arcuate distal section formed in a plane along a curvature, said prong element having a fluid passageway therein that is surrounded by a prong element sidewall, with the fluid passageway being in fluid communication with the barrel interior when said connector is fastened to the connector tip and having a port in said distal section that extends from the fluid passageway through said prong element sidewall whereby fluid received in the barrel interior when said plunger is in the withdrawn position may be ejected out of the port and onto the corneal surface by moving said plunger toward the depressed position.

34. A cannula for use in conjunction with a fluid source and operative to irrigate a corneal surface of an eye, comprising:
   (a) a connector adapted to attach to the fluid source, said connector oriented along a longitudinal axis; and
   (b) an elongated hollow prong element having a surrounding sidewall that includes a proximal end supported by said connector and a distal tip opposite said proximal end, said prong element including an arcuate distal section formed in a plane along a curvature, wherein said arcuate distal section has a first sidewall portion extending along a first radius of curvature to define a contact surface facing said longitudinal axis, and a second sidewall portion extending along a second radius of curvature that is larger than said first radius of curvature, and wherein said prong element has a fluid passageway therein that is surrounded by said sidewall with the fluid passageway being in fluid communication with the fluid source when said connector is fastened thereto, said prong element having a port in said distal section that extends from the fluid passageway through said sidewall whereby fluid from the fluid source may be ejected out of the port and onto the corneal surface during use.

35. A cannula according to claim 34 wherein said prong element is substantially inflexible.

36. A cannula according to claim 35 wherein said arcuate distal section extends along a fixed radius of curvature.

* * * * *